US005135866A

United States Patent [19]
Heifetz et al.

[11] Patent Number: 5,135,866
[45] Date of Patent: * Aug. 4, 1992

[54] VERY LOW PROTEIN NUTRIENT MEDIUM FOR CELL CULTURE

[75] Inventors: Aaron H. Heifetz, Columbia; James A. Braatz, Beltsville, both of Md.

[73] Assignee: W. R. Grace & Co. -Conn., New York, N.Y.

[ * ] Notice: The portion of the term of this patent subsequent to May 29, 2007 has been disclaimed.

[21] Appl. No.: 319,459

[22] Filed: Mar. 3, 1989

Related U.S. Application Data

[63] Continuation-in-part of Ser. No. 319,458, Mar. 3, 1989, Pat. No. 4,929,706, which is a continuation-in-part of Ser. No. 266,445, Nov. 2, 1988, Pat. No. 4,940,737.

[51] Int. Cl.$^5$ .................. C12N 5/00; C08G 18/08
[52] U.S. Cl. .............. 435/240.31; 435/240.3; 528/49
[58] Field of Search ............ 435/240.2, 240.3, 240.31, 435/240.1; 560/26; 528/60, 66, 49

[56] References Cited

U.S. PATENT DOCUMENTS

| | | | |
|---|---|---|---|
| 3,450,598 | 6/1969 | Welsh et al. | 435/240.23 |
| 3,723,393 | 3/1973 | Kistner | 260/77.5 B |
| 3,939,123 | 2/1980 | Matthews | 260/77.5 |
| 4,038,139 | 7/1977 | Birch | 435/240.3 |
| 4,072,565 | 2/1978 | Weiss et al. | 195/1.1 |
| 4,137,200 | 1/1979 | Wood et al. | 521/159 |
| 4,177,038 | 12/1979 | Biebricher et al. | 528/60 |
| 4,182,827 | 1/1980 | Jones | 528/60 |
| 4,226,935 | 10/1980 | Fusee | 528/60 |
| 4,241,537 | 12/1980 | Wood | 47/77 |
| 4,293,679 | 10/1981 | Cogliano et al. | 528/48 |
| 4,423,145 | 12/1983 | Stampfer | 435/240.3 |
| 4,439,585 | 3/1984 | Gould et al. | 525/127 |
| 4,443,546 | 4/1984 | Stemerman et al. | 435/240 |
| 4,452,893 | 6/1984 | Ng et al. | |
| 4,485,227 | 11/1984 | Fox | 528/67 |
| 4,560,655 | 12/1985 | Baker | |
| 4,569,981 | 3/1986 | Wenzel et al. | 528/67 |
| 4,657,866 | 4/1987 | Kumar | |
| 4,681,851 | 7/1987 | Baumgarten et al. | 435/262 |
| 4,767,704 | 8/1988 | Cleveland et al. | |
| 4,786,599 | 11/1988 | Chessebeuf et al. | |
| 4,851,346 | 7/1989 | Chan | 435/240.31 |
| 4,929,706 | 5/1990 | Heifetz et al. | 528/49 |
| 4,940,737 | 7/1990 | Braatz et al. | 521/103 |

FOREIGN PATENT DOCUMENTS 0248656 2/1988 European Pat. Off. .
0128112 12/1987 Japan .
8700248 8/1987 PCT Int'l Appl. .
WO88/00967 6/1988 PCT Int'l Appl. .

OTHER PUBLICATIONS

Velez et al., "Kinetics of Monoclonal Antibody Production in Low Serum Growth Medium", J. of Immun. Methods, vol. 86, pp. 45–52 (1986).
Schacter, "Serum Free Medium for Growth Factor Dependent and Independent Plasma Cytomas and Hybridomas", J. of Immon. Methods, vol. 99, pp. 259–270 (1987).
Mizrachi, "Primatone RL in Mammalian Cell Culture Media", Biotechnol. and Bioengineering, vol. 19, pp. 1557–1561 (1977).
Mizrahi, "Pluronic Polyols in Human Lymphocyte Cell Line Cultures", J. of Clinical Microbiol. vol. 2, pp. 11–13 (1975).
"Pluronic Polyols in Cosmetics", a brochure published by Wyandotte Chem. Corp. 1979.
Murhammer et al., "Scale-Up of Insect Cell Cultures: Protective Effects of Pluronic F-68" Biotechnology vol. 6, pp. 1411–1418.
Wolfe et al., Biotechniques, vol. 6, pp. 62–67 (1988).
Smith et al., J. Amer. Chem. Soc., vol. 81 (1959) pp. 161–163.
Farkas et al., Advan. Catalysis, vol. 13 (1962) pp. 434–439.
Ulrich et al., J. Org. Chem., vol. 32, pp. 3938–3941 (1967).
Freshney, "Culture of Animal Cells; A Manual of Basic Technique", Chapter 9, pp. 67–78 (1983).
Iscove et al., "Complete Replacement of Serum by Albumin, Transferrin, and Soybean Lipid in Cultures of Lipopolysaccharide-Reactive B Lymphocytes"; J. Exp. Med.; vol. 147/pp. 923–933 (1978).
Ham et al., "Media and Growth Requirements (I.A.5)"; Methods in Enzymology; (1978).
Barnes et al., "Methods for Growth of Cultured Cells in Serum-Free Medium"; Analytical Biochemistry; vol. 102/pp. 255–270 (1980).
McHugh et al., "Serum-Free Growth of Murine and Human Lymphoid and Hybridoma Cell Lines"; BioTechniques; pp. 72–77 (Jun. 1983).
KC Biological, "KC2000 TM Serum-Independent Medium"; Technical Informatoin Bulletin #24.
KC Biological, "KC2000 TM Serum-Independent Medium"; Technical Information Bulletin #25.
Ventrex, "Completely Defined Serum Free Media" (Brochure) (1984).

(List continued on next page.)

Primary Examiner—Douglas W. Robinson
Assistant Examiner—Susan M. Weber
Attorney, Agent, or Firm—Vanessa L. Appleby; Jill H. Krafte; Steven T. Trinker

[57] ABSTRACT

This nutrient medium is very effective for the serum-free or serum-protein-free culture of various animal cells, in both high and low density culture. Serum proteins have been replaced with non-protein-based cell growth enhancers and a non-serum derived protein supplement. The non-protein growth enhancer is a modified or derivatized polyurethane prepolymer of polymer and preferably is a sulfhydryl derivative of polyurethane. The protein supplement may be insulin, an insulin analog or an insulin-like growth factor.

12 Claims, No Drawings

OTHER PUBLICATIONS

Wolfe et al., "A New Serum-Free Medium for Monoclonal Antibody Production"; BioTechniques; vol. 6, No. 1/pp. 62–67; (1988).

Kane et al., "Protein-Free Culture Medium Containing Polyvinyl-Alcohol, Vitamins, and Amino-Acids Supports Development of Eight-Cell Hamster Embryos to Hatching Blastocysts," *Journal of Experimental Zoology*, vol. 247, pp. 183–187 (1988).

Wolfe et al., "Continuous Culture of Rat C6 Glioma in Serum-Free Medium", Journal of Cell Biology; vol. 87/pp. 434–441 (1980).

Barnes et al., "Serum-Free Cell Culture: a Unifying Approach"; Cell; vol. 22/pp. 649–655 (Dec., 1980).

Wolfe et al., "Continuous Serum-Free Culture of the N18TG-2 Neuroblastoma x Glioma Hybrid Cell Lines"; Cold Spring Harbor Conferences on Cell Proliferation; vol. 9/pp. 1075–1088 (1982).

VERY LOW PROTEIN NUTRIENT MEDIUM FOR CELL CULTURE

This is a continuation-in-part of U.S. Pat. No. 319,458, filed Mar. 3, 1989, now U.S. Pat. No. 4,929,706, which is a continuation-in-part of U.S. Ser. No. 266,445, filed Nov. 2, 1988, now U.S. Pat. No. 4,940,737.

BACKGROUND OF THE INVENTION

This invention relates generally to a medium for the in vitro culture of animal cells. More specifically, the invention is a defined nutrient medium capable of supporting serum-free culture. Further, serum-derived proteins typically present in defined (i.e., serum free) media may be replaced with non-protein-based cell growth enhancers and a protein supplement which is non-serum-derived. This unique medium has been designed specifically for supporting animal cell growth without supplementation with serum or serum-derived proteins Excellent cell growth is achieved and the medium is of a wide variety of cell lines and cell types.

For in vitro culture, a medium must, of course, supply all essential nutrients for the cells: vitamins, amino acids, lipids, nucleic acid precursors, carbohydrates, trace elements, and bulk ions. Historically, basal nutrient media were designed to support cell growth only after being supplemented with a biological extract, e.g., serum or embryo extracts. Serum, in particular, proved to be an effective supplement, presumably because it contains the necessary growth- and multiplication-promoting factors in physiologically acceptable concentrations. Examples of basal nutrient media of this type are Eagle's basal medium (BME), the composition of which is recited in U.S. Pat. No. 3,450,598 (Welsh et al.), and Dulbecco's Modified Eagle's (DME) medium, the composition of which is recited in Table II of Ham et al., "Media and Growth Requirements," Methods of Enzymology, (1978). DME medium, which contains relatively high concentrations of the essential amino acids and sugars, is representative of the commercially available media formulated for the mass culture of cells with serum supplementation.

With growing sophistication in cell culture techniques, factors present in serum or other biological extracts have been identified. It is now possible to grow mammalian cells in a serum-free environment, by supplementing a basal nutrient medium with defined proteins necessary for cell growth and multiplication. Ham's F12 medium, the composition of which is given in Table II of Ham et al., supra, contains low concentrations of the essential amino acids and sugars, and includes lipids, nucleic acid derivatives, vitamins and nonessential amino acids.

It is now generally accepted that a readily obtainable and sufficiently complex basal nutrient medium for mass culture of cells in low serum concentrations can be fabricated by mixing DME and F12 media. Such mixtures, when supplemented with the appropriate protein factors, can also support the serum-free growth of many cell types. Barnes et al., "Methods for Growth of Cultured Cells in Serum-Free Medium," Analytical Biochem., Vol. 102, pp. 255-70 (1980), describes examples of both approaches.

Several commercially available nutrient media are based on mixtures of DME, F12 and/or other media such as those listed in Table II of Ham et al., supra. However, simple mixtures of existing commercial media are by no means optimal for culturing all cell lines and medium preparations therefore have been targeted largely to particular cell lines or cell types. Wolfe et al., "Continuous Culture of Rat C6 Glioma in Serum-Free Medium," J. Cell Biol, Vol. 87, pp. 434-41 (1980), teaches the use of a 3:1 DME-to-F12 mixture, supplemented with trace elements, and further supplemented with the following defined proteins insulin, transferrin, fibroblast growth factor, linoleic acid complexed to fatty acid-free bovine serum albumin, and serum-spreading factor (vitronectin). Similarly, a serum-free basal nutrient medium is disclosed in U.S. Ser. No. 029,577, "Basal Nutrient Medium for Cell Culture," (Wolfe), filed Mar. 24, 1987, which is supplemented with defined proteins such as albumin, iron-saturated transferrin, insulin, vitronectin and fibroblast growth factor.

With the increasing use of cultured mammalian cells to produce biologicals (e.g., monoclonal antibodies and genetically engineered proteins), there is an increasing demand for chemically defined, serum-free media. Purification of the desired cellular product is greatly complicated by the presence of serum or serum-proteins. It is therefore desired to reduce the protein content of the culture medium to a few defined compounds from which the monoclonal antibody or other cellular product can be separated more readily. It is also desired to reduce the protein content of the media as much as possible.

SUMMARY OF THE INVENTION

The nutrient medium of the present invention is suitable for use without supplemental serum or serum-derived proteins Moreover, non-protein cell growth enhancers have replaced several previously required supplemental proteins. The resulting very low protein media equal or outperform prior art media which employ serum or high protein level supplementation.

The primary objective of this invention is to provide a chemically defined medium which supports cell culture in the absence of serum or serum-derived proteins. One important intended benefit is reduction of the concentrations of growth inhibitors that are present in serum. It is a specific object to replace commonly used serum-protein supplements (albumin and transferrin) with non-protein compounds and/or with non-serum derived protein supplements. In addition, by providing a culture medium with very low levels of exogenous protein, recovery and purification of the desired cell product will be facilitated. A secondary object is to provide culture media which can be used with very low levels of serum or serum-derived proteins, if desired.

It is an additional goal to provide a cell culture medium particularly well suited for use in hollow fiber bioreactors.

It is a further object to design a medium having nutrients at levels which are suitable for high cell densities, but which are not inhibitory for low density culture. It is intended to eliminate the need for media changes when going from low to high density culture conditions, as well as to reduce or eliminate the need for "weaning" cells from serum-supplemented to serum-free media.

Still another object of the invention is to design a nutrient medium which is suitable for the culture of a wide variety of cell types and sources. It is intended that this medium be compatible with the clonal growth of animal cells.

A more specific object is to design a medium compatible with high levels of immunoglobulin production by hybridoma cells. It is also intended that the medium be free of polypeptides which co-purify with immunoglobulins. It is a goal of this invention to markedly improve the purity of the cellular product recovered from the culture.

DETAILED DESCRIPTION OF THE INVENTION

The nutrient medium described herein comprises appropriate levels of essential and non-essential amino acids and amino acid derivatives, bulk ions and trace elements, buffers, vitamins, coenzymes, energy sources, novel synthetic growth factors, nucleic acid derivatives and lipids to function as an all-purpose nutrient medium for in vitro animal cell culture. The medium is designed to be used either without serum or serum-derived protein supplementation (although very low levels of serum or other biological extracts such as egg hydrolysates, protease peptone, plasma, etc., can be added, if desired). The protein requirements are met by the presence of insulin (or insulin analogs or insulin-like growth factors) and non-protein-based cell growth enhancing compositions.

The medium described herein is an all-purpose nutrient medium. It has been demonstrated to effectively support both low and high density cell culture. It has been demonstrated to supply the nutrients needed by a variety of cell lines and types. The medium gives unexpectedly good performance in supporting the production of monoclonal antibodies in a variety of production modes, such as hollow fiber bioreactors, fermentors, spinner flasks and roller bottles. High purity cell products, e.g. monoclonal antibodies, are readily recoverable.

It now has been found that certain commonly used protein supplements can be successfully replaced with non-protein growth enhancers. The present medium eliminates the need for both albumin and transferrin protein supplementation. Transferrin is replaced with one or more alternative supplemental iron sources. Albumin is replaced with a modified polyurethane prepolymer- or polymer-based cell growth enhancer. Insulin is the only supplemental protein necessary with the media of the present invention.

The components described herein and listed in Table I are given in the physical and ionization states common in the art of media preparation. However, other physical and/or ionization states may be used, if desired. The concentration of any of the components, with the exception of HEPES and sodium hydroxide, may be varied from that listed in Table I by as much as a factor of two as long as the osmolarity, pH and sodium-to-potassium ratio are within the ranges described herein. The HEPES concentration can range from about 10.0 to about 28.0 mM. The quantity of NaOH used is a function of the pH selected.

Bulk Ions and Trace Elements — Bulk ions are necessary for cell growth and for maintenance of membrane potentials and osmotic balance. They also play co-factor roles in enzymatic reactions. Sodium, potassium, calcium, magnesium, chloride, phosphate, and sulphate all perform important functions in normal cell metabolism. The specific sodium-to-potassium ratio in the medium, important in regulating transmembrane potential, is discussed further below. Bicarbonate or carbon dioxide is also necessary, and must be provided in the culture medium for low density cell culture. In high density cell culture, the cells themselves may generate sufficient levels, without the need for exogenous bicarbonate and carbon dioxide. Trace inorganic elements (iron, zinc, selenium, silicon, vanadium, copper, nickel and molybdenum) are necessary for the function of many enzymes (e.g., $Se^{++}$ in glutathione reductase). Trace inorganic elements also can directly modulate transmembrane signaling events (e.g., vanadate modulation of insulin responsiveness). The specific compounds listed in Table I are commonly used in media preparations and are preferred here because the indicated hydration states are advantageous for the stability of the powdered form of the medium of this invention. Substitutions may be made by those of ordinary skill in the art.

Ferric sulfate ($Fe_2(SO_4)_3$) is used in the media of this invention as a replacement for the serum-derived protein transferrin. Thus, the addition of a single inorganic compound serves the growth support and enhancement functions of the protein. Other inorganic iron sources may be used including, for example, ferric citrate and ferrous fumarate. Ferrous sulfate is not suitable for use in this medium.

Amino Acids — The following essential amino acids are included in this medium: L-arginine (L-Arg), L-cysteine (L-Cys), L-glutamine (L-Gln), L-histidine (L-His), L-hydroxyproline (L-Hydroxy-Pro), L-isoleucine (L-Ile), L-leucine (L-Leu), L-lysine (L-Lys), L-methionine (L-Met), L-phenylalanine (L-Phe), L-threonine (L-Thr), L-tryptophan (L-Trp), L-tyrosine (L-Tyr), and L-valine (L-Val). In addition, the following non-essential amino acids are included: L-alanine (L-Ala), L-asparagine (L-Asn), L-aspartic acid (L-Asp), L-glutamic acid (L-Glu), glycine (Gly), L-proline (L-Pro) and L-serine (L-Ser). In addition, the amino acid derivatives glutathione and putrescine are present in the medium of this invention. Again, the forms listed in Table I are preferred, particularly for the preparation of a powdered medium that will dissolve readily. For preparation of a liquid medium, alternative forms of these amino acids may be selected.

Vitamins/Coenzymes — A number of water soluble vitamins and co-enzymes are known to aid cell culture. Biotin, pantothenic acid, folic acid, folinic acid, niacinamide (nicotinamide), p-aminobenzoic acid, pyridoxal, pyridoxine, riboflavin, thiamine and vitamin $B_{12}$ are utilized in this medium.

Energy Sources — Glucose, pyruvate and glutamine are utilized as the energy and carbon sources in the present medium. Pyruvate is provided as sodium pyruvate. It may be desired for process control to alter the components used by the cells as an energy source. For example, the glucose may be substantially lowered or replaced by galactose or fructose, and the glutamine concentration varied.

Nucleic Acid Derivatives — Adenine and hypoxanthine are provided as sources of purines. Thymidine is provided as a source of pyrimidines.

Lipids — The formulation of this invention includes the following lipids, lipid precursors and lipid derivatives: choline, ethanolamine, i-inositol, linoleic acid and lipoic acid. Additional lipids and other derivatives such as methyl lineolate may be added or substituted as required for particular cell types. Ethanolamine is a major component in the membrane phospholipid biosynthetic pathway.

Buffers — The buffer system of the nutrient medium described herein offers the operator the ease and flexibility of using air equilibration for pH control. This is an important aspect of the present invention, since the medium is primarily intended for serum-free or very low serum concentration culture. It has been found that when the serum concentration is reduced, the levels of bicarbonate normally suitable for pH control in equilibrium with 10% carbon dioxide/air become inhibitory. The present buffer system also offers an alternative to the burdensome adjustment of carbon dioxide concentrations which previously have been required for maintaining the pH within physiologically compatible ranges.

The buffer system utilizes sodium bicarbonate, HEPES (n-2-hydroxyethylpiperazine-N'-2-ethanesulfonic acid), sodium hydroxide and carbon dioxide. The small quantities of carbon dioxide required for cellular metabolism in low density cultures are provided in the medium of this invention via equilibration of atmospheric carbon dioxide and the $HCO_3^-$ present in the medium. For high density cultures, sufficient carbon dioxide is produced via normal cell metabolism.

The need for using the pH indicator phenol red is eliminated in the medium of this invention, since the buffer system of this medium will maintain the pH within physiological ranges under common culture conditions in an air-equilibrated system. This is extremely advantageous in terms of purifying the desired cellular product, since phenol red binds to proteins, changing their chromatographic behavior. In addition, phenol red may affect cellular biosynthesis and metabolism. Elimination of phenol red is therefore significant in terms of reducing the required purification steps and increasing recoverable product.

The medium may be formulated at about pH 7.0 to about pH 7.4 at 37° C. Formulation at a higher pH, for example, at about pH 8.0, may be employed as a process control strategy for continuously fed bioreactors to neutralize the lactic acid produced by the cultured cells, instead of adding additional base as a process control strategy. When the medium is to be used in a hollow fiber bioreactor, formulation at about pH 7.35 (37° C) is preferred. A pH of 7.2 (37° C) is preferred for other uses.

Polymeric Cell Growth Enhancers

One or more cell growth enhancers which comprise a modified polyurethane polymer are used in the media of this invention. The cell growth enhancers of this invention are prepared by modifying or derivatizing isocyanate end-capped polyols so that a free amino, sulfonic acid or sulfhydryl functional group is expressed on the modified prepolymer or polymer. These cell growth enhancers, and procedures for their preparation, are described in detail in U.S. Ser. No. 319,458, "Cell Growth Enhancers and/or Antibody Production Stimulators Comprising Chemically Modified Hydrophilic PolyureaUrethane Prepolymers and Polymers," (Heifetz et al.), filed Mar. 3, 1989, now U.S. Pat. No. 4,929,706, and incorporated by reference herein. A brief description of the polymeric cell growth enhancers and their preparation follows.

Prepolymer Preparation

The prepolymers utilized as the base for the cell growth enhancers are prepared from oxyalkylene-based alcohols. These can be diols or polyols, including diols or polyols made up of ethylene oxide monomer units, and to some extent monofunctional alcohols made up of the same monomer units. Prepolymers are formed when the diols and/or polyols are end-capped with di or polyfunctional isocyanates.

One extensive class of hydrophilic, isocyanate-capped urethane prepolymer is described in U. S. Pat. No. 4,137,200 (Wood et al.), the teachings of which are incorporated herein. The Wood et al. prepolymers are blends of a monomeric polyol and polyoxyalkylene glycol, the hydroxyl groups of the blend being capped with a polyisocyanate.

A second class of prepolymers suitable for preparation of the cell growth enhancers comprises polyoxyalkylene diols or polyols which are of generally higher molecular weights than the Wood et al. prepolymers, and which are predominantly or exclusively made up of ethylene oxide units. This second class is somewhat more preferred for use in cell growth enhancers in the media of this invention. Preferably, at least 75% of the monomer units should be ethylene oxide. As in Wood et al., the diols or polyols are end-capped with di- or polyfunctional isocyanates. As specific examples of this class of prepolymers, prepolymers from the BIOPOL™ polyurethane prepolymer series available from Grace Specialty Chemicals Co., W. R. Grace & Co.-Conn., will be particularly suitable.

Modifying Compounds

The polyurethane-based cell growth enhancer is prepared by modifying or derivatizing the above described prepolymers. The prepolymers are modified so that they express sulfhydryl, sulfonic acid or amino functional groups. These are referred to herein as sulfhydryl derivatives, sulfonic acid derivatives and amino derivatives, respectively.

The prepolymer is modified, or derivatized, by reacting it with a compound containing at least one isocyanate (NCO) reactive functional group. The NCO reactive functional group acts as the attachment point between the prepolymer and the modifying compound. The modifying compound also has a second functional group which may be isocyanate reactive, but is preferably less reactive so that the isocyanates are modified by the first NCO reactive functional group. Upon modification of the isocyanate group, a "free" functional group (that is, the second functional group of the modifying compound) is expressed. Alternatively, the second functional group can be expressed subsequent to the prepolymer modification as the result of internal bonds being reduced or broken.

Sulfhydryl derivatives of polyurethanes are preferred. In these derivatives, the modified prepolymer or polymer expresses —SH. A preferred polymeric cell growth enhancer is a cysteamine-modified polyurethane polymer. Such a growth enhancer may be formed by treating cystamine (($NH_2CH_2CH_2$)$_2S_2$) with a reducing agent, thereby forming cysteamine ($NH_2CH_2CH_2SH$) which contains both a free amino and a free sulfhydryl group. The amino and sulfhydryl groups of the cysteamine molecule interact to cause formation of the thiolate ion. The NCO groups of the prepolymer react preferentially with the thiolate group of the self-catalyzed cysteamine molecule, yielding a prepolymer modified via the thiolate so as to have a free amino group expressed by the modified prepolymer.

Alternatively, cystamine itself can be reacted with the prepolymer prior to reduction of the disulfide bond. In this case, both the NCO reactive functional group and the free functional group expressed on the modified prepolymer are —$NH_2$. However, the free functional group is changed from —$NH_2$ to —SH by reducing the disulfide bond in cystamine to express the sulfhydryl group.

Another sulfhydryl derivative is a thiopropionic acid-modified polyurethane. Such a derivative also exhibits growth enhancement properties.

Sulfonic acid derivatives similarly function to increase cell growth. For example, taurine may be used as the modifying compound. Alternatively, amino-modified polyurethanes may be used as cell growth enhancers.

The cell growth enhancers described herein are water soluble. After solutions of these polymeric units have been dialyzed and filter sterilized, the cell growth enhancer is ready for addition to the cell culture media described herein. The cell growth enhancer is generally used in concentrations between 10 and 50 $\mu$g/ml, depending on the cell line and medium used.

Osmolarity — The sodium/potassium ratio and total osmolarity of the medium have been adjusted for compatibility with high levels of murine immunoglobulin production. The preferred sodium-to-potassium ratio is about 30, but may range from about 25 to about 35. The osmolarity of the medium is low, about 285 to about 315 mosm, preferably about 295 to about 305 mosm.

The medium described herein is particularly well suited for the production of monoclonal antibodies in hollow fiber bioreactors, fermentors, spinner flasks and roller bottles. The high levels of gas exchange routinely employed in these types of culture are compatible with the present formulation. The osmolarity of the medium has been kept low to allow for some rise during culture, while still maintaining the osmolarity within ranges suitable for maintaining healthy, productive cells. For use in hollow fiber reactors, the medium preferably is reconstituted at about 295 mosm. In addition, biocompatible reducing agents, such as glutathione have been included in the medium to compensate for potential oxidative complications arising from these high levels of gas exchange.

The formulation for the nutrient medium of this invention is listed in Table I. Quantities of the components are given in molarity as well as concentration. The formulation of Table I is the preferred embodiment of this invention. The quantity of each component may be varied by a factor of 2, that is, the quantity of each component may vary from about 50% to about 200% of the quantity listed in Table I. The concentrations for each component have been selected on the basis of the mechanism by which it enters the cell, i.e., active or passive transport, and the concentrations required to achieve sufficient transport for the desired level of biological activity.

The hydration state of the individual components and the prepared basal nutrient medium may be varied according to convenience. The hydration states given herein are those which are commonly used in the art of media preparation. However, as a practical matter, it is preferred to have the prepared medium be as dry as possible.

The nutrient medium as described above may be formulated and packaged as a dry or concentrated preparation for reconstitution prior to use. In the preferred embodiment of this invention, the medium is prepared as a dry powder, comprising the first sixty-one components listed in Table I.

TABLE I

| COMPONENT | MW | M | mg/L |
|---|---|---|---|
| Bulk Ions & Trace Elements | | | |
| 1. $CaCl_2.2H_2O$ | 147.02 | $1 \times 10^{-3}$ | 147.02 |
| 2. $CuSO_4.5H_2O$ | 249.68 | $3 \times 10^{-9}$ | 0.000749 |
| 3. $FeSO_4.7H_2O$ | 278.02 | $1 \times 10^{-6}$ | 0.278 |
| 4. $Fe(NO_3)_3.9H_2O$ | 404.02 | $2 \times 10^{-7}$ | 0.0808 |
| 5. KCl | 74.55 | $4 \times 10^{-3}$ | 298.2 |
| 6. $MgSO_4.7H_2O$ | 246.38 | $8 \times 10^{-4}$ | 197.1 |
| 7. NaCl | 58.44 | $1.05 \times 10^{-1}$ | 6136.2 |
| 8. $Na_2HPO_4.7H_2O$ | 268.1 | $3 \times 10^{-4}$ | 80.43 |
| 9. $NaH_2PO_4.2H_2O$ | 156.01 | $6 \times 10^{-4}$ | 93.606 |
| 10. $Na_2SeO_3.5H_2O$ | 263.01 | $3 \times 10^{-8}$ | 0.00789 |
| 11. $Na_2SiO_3.9H_2O$ | 284.2 | $1 \times 10^{-5}$ | 2.842 |
| 12. $(NH_4)_6Mo_7O_{24}.4H_2O$ | 1235.9 | $3 \times 10^{-9}$ | 0.00371 |
| 13. $NH_4VO_3$ | 116.99 | $5 \times 10^{-10}$ | 0.0000585 |
| 14. $NiSO_4.6H_2O$ | 262.80 | $3 \times 10^{-10}$ | 0.0000788 |
| 15. $ZnSO_4.7H_2O$ | 287.54 | $8 \times 10^{-7}$ | 0.23 |
| 16. $Fe_2(SO_4)_3$ | 400.60 | $5 \times 10^{-5}$ | 20.0 |
| Essential Amino Acids | | | |
| 17. L-Arg | 210.7 | $8 \times 10^{-4}$ | 168.56 |
| 18. L-Cys HCl.$H_2O$ | 175.6 | $3 \times 10^{-4}$ | 52.68 |
| 19. L-Gln | 146.1 | $5 \times 10^{-3}$ | 730.5 |
| 20. L-His HCl.$H_2O$ | 209.7 | $2 \times 10^{-4}$ | 41.94 |
| 21. L-Hydroxy-Pro | 131.13 | $1 \times 10^{-4}$ | 13.113 |
| 22. L-Ile | 131.2 | $6 \times 10^{-4}$ | 78.72 |
| 23. L-Leu | 131.2 | $6 \times 10^{-4}$ | 78.72 |
| 24. L-Lys HCl | 182.7 | $8 \times 10^{-4}$ | 146.16 |
| 25. L-Met | 149.2 | $1 \times 10^{-3}$ | 149.2 |
| 26. L-Phe | 165.2 | $3 \times 10^{-4}$ | 49.56 |
| 27. L-Thr | 119.1 | $6 \times 10^{-4}$ | 71.46 |
| 28. L-Trp | 204.2 | $6 \times 10^{-5}$ | 12.252 |
| 29. L-Tyr (di$Na^+$)2$H_2O$ | 263.2 | $3 \times 10^{-4}$ | 78.95 |
| 30. L-Val | 117.2 | $6 \times 10^{-4}$ | 70.32 |
| Nonessential Amino Acids | | | |
| 31. L-Ala | 89.09 | $2 \times 10^{-5}$ | 1.782 |
| 32. L-Asn.$H_2O$ | 150.1 | $3 \times 10^{-4}$ | 45.03 |
| 33. L-Asp | 133.1 | $2 \times 10^{-5}$ | 2.662 |
| 34. L-Glu | 147.1 | $2 \times 10^{-5}$ | 2.942 |
| 35. Gly | 75.07 | $3 \times 10^{-5}$ | 2.252 |
| 36. L-Pro | 115.1 | $2 \times 10^{-4}$ | 23.02 |
| 37. L-Ser | 105.1 | $3 \times 10^{-4}$ | 31.53 |
| Amino Acid Derivatives | | | |
| 38. Glutathione | 307.3 | $1 \times 10^{-6}$ | 0.307 |
| 39. Putrescine 2HCl | 161.1 | $3 \times 10^{-7}$ | 0.048 |
| Water Soluble Vitamins and Co-Enzyme | | | |
| 40. Biotin | 244.3 | $3 \times 10^{-8}$ | 0.007 |
| 41. D-Ca pantothenate | 238.3 | $2 \times 10^{-5}$ | 4.766 |
| 42. Folic acid | 441.41 | $6 \times 10^{-6}$ | 2.648 |
| 43. Folinic acid ($Ca^+$).5$H_2O$ | 601.6 | $1 \times 10^{-6}$ | 0.602 |
| 44. Niacinamide (Nicotinamide) | 122.1 | $3 \times 10^{-5}$ | 3.663 |
| 45. p-Aminobenzoic acid | 137.14 | $3 \times 10^{-6}$ | 0.411 |
| 46. Pyridoxal HCl | 203.6 | $1 \times 10^{-5}$ | 2.036 |
| 47. Pyridoxine HCl | 205.6 | $3 \times 10^{-7}$ | 0.062 |
| 48. Riboflavin | 376.4 | $8 \times 10^{-7}$ | 0.301 |
| 49. Thiamine HCl | 337.0 | $9 \times 10^{-6}$ | 3.036 |
| 50. Vitamin B12 | 1355.4 | $3 \times 10^{-7}$ | 0.407 |
| Energy Sources | | | |
| 51. D-Glucose | 180.16 | $2 \times 10^{-2}$ | 3603.2 |
| 52. Na Pyruvate | 110.0 | $1 \times 10^{-3}$ | 110.0 |
| Nucleic Acid Derivatives | | | |
| 53. Adenine | 135.13 | $1 \times 10^{-6}$ | 0.135 |
| 54. Hypoxanthine ($Na^+$) | 146.1 | $7 \times 10^{-6}$ | 1.0227 |
| 55. Thymidine HCl | 279.3 | $1 \times 10^{-5}$ | 3.373 |
| Lipids and Derivatives | | | |
| 56. Choline chloride | 139.63 | $1 \times 10^{-4}$ | 13.96 |
| 57. Ethanolamine HCl | 97.55 | $2 \times 10^{-5}$ | 1.951 |
| 58. i-Inositol | 180.2 | $1 \times 10^{-4}$ | 18.02 |
| 59. Linoleic acid | 280.4 | $1 \times 10^{-7}$ | 0.028 |
| 60. Lipoic acid | 206.3 | $2 \times 10^{-7}$ | 0.041 |
| Buffers | | | |
| 61. HEPES | 238.3 | $2.5 \times 10^{-2}$ | 5957.5 |
| 62. NaOH | 40.01 | $1.23 \times 10^{-2}$ | 492.12 |
| 63. $NaHCO_3$ | 84.01 | $3 \times 10^{-3}$ | 252.03 |
| Synthetic Growth Factors | | | |
| 64. Insulin | 6000 | $8.4 \times 10^{-7}$ | 5.0 |
| 65. Modified | — | $1.7 \times 10^{-6}$ | 25.0 |

TABLE I-continued

| COMPONENT | MW | M | mg/L |
|---|---|---|---|
| Polyurethane | | | |

The remaining components are then added when the dry medium is reconstituted. Reconstitution may be done just prior to use. Alternatively, the medium may be reconstituted and packaged. The shelf life of this medium as a dry powder stored at about 4° C. is at least several years. The liquid medium, either as prepared or as reconstituted from the dry powder is less stable, but when stored at about 4° C. is stable for about two months or more.

Reconstitution may be performed by adding concentrated stocks of bicarbonate, base or other of the medium components, so long as the relative concentrations described above and indicated in Table I are present. If those components are added as solids, reconstitution is accomplished by the addition of sterile, de-ionized tissue culture grade water. The medium is sterilized prior to use. A protocol for reconstituting the powdered medium is detailed in Example I.

As stated above, the nutrient medium of this invention is designed to be used in the absence of any supplementation with serum or serum-derived proteins. The medium will, however, continue to support cell growth and metabolism when supplemented with low levels of serum or with additional proteins, as appropriate for the particular cell line being cultured. That is, the addition of serum is not necessarily harmful, and considerably lower levels of serum may be used to supplement the medium of this invention for enhancement of growth or antibody production than are typically used with the prior art media. For example, very low levels of serum, preferably less than about one percent by volume, may be used.

The medium described herein can be used for serum-free cell culture when supplemented with the non-protein growth factors described above and with insulin. Insulin or insulin analogs may be present in concentrations of about 1.0 to about 10.0 μgm/ml, preferably about 5.0 μgm/ml. Insulin-like growth factors may be present in lower concentrations, sufficient to maintain cell growth (e.g., a concentration of about 10.0 to about 250.00 ngm/ml may be sufficient for IGF-I). Supplementing the nutrient medium in this manner has been found to be excellent for both high and low density cell culture. Of course, additional proteins, such as bovine serum albumin, low density lipoprotein, etc., may be added if desired.

The examples which follow are given for illustrative purposes and are not meant to limit the invention described herein. The following abbreviations have been used throughout in describing the invention:

| BSA | bovine serum albumin |
|---|---|
| °C. | degree(s) Centigrade |
| cm$^2$ | cubic centimeter(s) |
| DME | Dulbecco's Modified Eagle's |
| gm | gram(s) |
| L | liter(s) |
| M | molar |
| mM | millimolar |
| mg | milligram(s) |
| min | minute(s) |
| ml | milliliter(s) |
| mosm | milliosmolality (mmol/Kg) |
| MW | molecular weight |
| N | normal |
| ngm | nanogram(s) |
| nm | nanometer(s) |
| osm | osmolality (mol/Kg) |
| μ | micro- |
| PBS | phosphate buffered saline |
| % | percent |
| rpm | revolution(s) per minute |
| v | volume |
| wt | weight |

EXAMPLE I (Preparation of Medium)

Powdered Medium — The medium was prepared by mixing components 1-15 and 17-61, in the quantities listed in Table I. The ingredients were milled to form a dry powder.

Stock Solutions (1) Bicarbonate/base (NaHCO$_3$/NaOH) stock solution was prepared by adding 17.922 gm NaHCO$_3$ to 711.2 ml of a 1.00 N solution of NaOH. The volume was then adjusted to one liter.

(2) Ferric sulfate stock solution was prepared by dissolving 2.0 gm Fe$_2$(SO$_4$)$_3$ in 100.0 ml water.

(3) Insulin stock solution was prepared by dissolving bovine insulin (INS) (Sigma I5500) at 1000-fold the concentration in the final preparation. For 100.0 ml stock, 500.0 mg INS were dissolved in a solution of 0.05 M HCl in PBS (using 1.0N HCl and 10X PBS (Dulbecco's Ca++-, Mg++-free) (GIBCO/BRL)). The stock was filter sterilized and stored at 4° C.

(4) Modified polyurethane growth factor stock solution was prepared as follows:

A prepolymer was prepared by mixing 848.8 gm of deionized and dried polyol BASF 1123 (BASF) with 91.6 gm isophorone diisocyanate in a one liter polyethylene bottle at room temperature with mechanical stirring for 30 minutes. Dry nitrogen was purged over the mix and the bottle was sealed with a screw cap and placed in an electric oven at 125° C. After 11 days the reaction was terminated. The product had an isocyanate value of 0.43 meq/gm and a viscosity of 62,000 cps at 25° C.

Excess cystamine was added to insure that all the isocyanates on the prepolymer were endcapped. Cystamine, 1.5 gm, (Aldrich lot no. 02016cj) was dissolved in 150 ml of 50 mM sodium bicarbonate, pH 8.5. This solution was added to 10.0 gm of prepolymer and stirred. A gel did not form, therefore the assumption was made that the fourfold excess cystamine capped all the isocyanate groups, thus preventing crosslinking. While stirring, 0.6 ml of mercaptoethanol was added to the cystamine/prepolymer solution to reduce the cystamine to cysteamine. After dialyzing in deionized water, 55 mM mercaptoethanol solution in PBS was added and the mixture was stirred. The product was filter sterilized through a 0.2 micron filter.

Reconstitution and Supplementation of Powdered Medium

Six liters of tissue culture grade water were placed in a 10.0 liter vessel, to which a 195.7 gm quantity of the powdered medium (a ten liter-equivalent) was added. The package was rinsed twice with 100.0 ml aliquots of water. Next, 150.0 ml (15.0 ml/L of medium) of the bicarbonate/base stock solution was added to the vessel. The sides of the vessel were rinsed with 630.0 ml water to insure that all the powder dissolved. Three liters of water were added to bring the volume to 10.0 L.

The pH of the reconstituted medium was determined (at 37° C.) to be 7.18 ± 0.03 with a blood gas analyzer (Corning). The osmolarity was determined to be 295 ± 5.0 mosm by vapor pressure osmometry (Wescor).

The reconstituted medium was filter sterilized using a Masterflex(TM) pump (#25 head) (Cole-Parmer) at approximately 500.0 ml/min. The solution was passed through a Milli-stack GS (TM) filter (Millipore MSG-S05C22) into sterile glass and polycarbonate carboys. A 10.0 ml (1.0 ml/L of medium) aliquot of each of the ferric sulfate, insulin and modified polyurethane stock solutions was added.

The reconstituted medium was tested to verify sterility and ability to promote cell proliferation. A 10.0 ml aliquot of medium was sterilely placed in a tissue culture flask (T-75) to which one million HFN 7.1 murine hybridoma cells (CRL 1606, obtained from the American Type Culture Collection (ATCC), 12301 Parklawn Drive, Rockville, Md. 20852) were added. A 100 L aliquot then was diluted with 10.0 ml PBS and the cell concentration determined using a Coulter Counter (TM) particle counter (Coulter Electronics). The flask was tightly clasped and incubated at 37° C. for 24 hours. At least 200,000 cells/ml were observed, indicating the ability of the medium to support the culture.

A test sample of the bottled medium was left at 37° C. overnight to verify sterility. No cloudiness or other evidence of microbial contamination was observed. The medium was then stored at 4° C.

EXAMPLE II

This example compares cell growth in four media: the serum-free medium of Example I, the serum-free medium of Example I supplemented with the proteins BSA and transferrin, and a commercially available medium, WRC 935 ™ basal nutrient medium (Amicon Division, Grace Specialty Chemicals Co., W. R. Grace & Co.-Conn.), both with and without supplemental BSA and transferrin. WRC 935 medium, as commercially available, includes a protein supplement of 5.0 μg/ml insulin, 50.0 μg/ml BSA and 5.0 μg/ml transferrin. It was used in this example both as sold and without BSA and transferrin. Better cell growth was seen with the medium of this invention (that is, the serum-free medium of Example I).

An aliquot of cells of the murine hybridoma line HFN 7.1 was inoculated at Day 0 into roller bottles containing one of the four media. The bottles were tightly sealed. The bottles were placed in an incubator at 37° C. on a roller apparatus at about 1.5 rpm.

Aliquots of each culture were removed daily and the cell concentrations were determined with a Coulter Counter ™ particle counter (Coulter Electronics). Cell viability was determined by the trypan blue dye exclusion assay (Sigma Chemical Co.) The results are shown in Table II.

The cells were removed from each daily aliquot by filtration. The conditioned medium supernatant from each aliquot was stored at 20° C. until termination of the experiment.

TABLE II

| | Cell Number ($\times 10^{-4}$) | | | | | |
|---|---|---|---|---|---|---|
| Medium | Day 0 | Day 3 | Day 4 | Day 5 | Day 6 | Day 7 |
| WRC 935 Medium (including 50.0 μg/ml insulin, 50.0 μg/ml BSA and 5.0 μg/ml transferrin) | 2.0 | 3.1 | 8.4 | 21.0 | 45.0 | 67.0 |
| WRC 935 Medium (including 5.0 μg/ml insulin, but without BSA and transferrin) | 2.0 | 0.7 | 0.4 | 0.4 | 0.8 | 0.8 |
| Example I Medium | 2.0 | 1.6 | 6.0 | 10.0 | 30.0 | 74.0 |
| Example I Medium (plus 50.0 μg/ml BSA and 5.0 μg/ml transferrin) | 2.0 | 13.0 | 42.0 | 69.0 | 94.0 | 100.0 |

EXAMPLE III

This example compares cell growth in the serum-free medium of Example I with commercially available WRC 935 medium (including protein supplements (5.0 μg/ml insulin, 50.0 μg/ml BSA and 5.0 μg/ml transferrin)), where both media have been supplemented with 50.0 μM monothioglycerol to demonstrate that the addition of monothioglycerol (a sulfhydryl reducing agent) does not itself effect relative media performance. The procedures of Example II were followed. The results are shown in Table III. The medium of this invention demonstrated equivalent performance to that of the commercially available medium, notwithstanding elimination of the serum-derived proteins BSA and transferrin.

TABLE III

| | Cell Number ($\times 10^{-4}$) | | | | |
|---|---|---|---|---|---|
| Medium | Day 0 | Day 4 | Day 5 | Day 6 | Day 7 |
| WRC 935 Medium | 2.0 | 13.0 | 31.0 | 58.0 | 72.0 |
| Example I Medium | 2.0 | 11.0 | 27.0 | 59.0 | 81.0 |

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. A nutrient medium for in vitro animal cell culture, consisting essentially of the following:

| | |
|---|---|
| $CaCl_2 \cdot 2H_2O$ | $1 \times 10^{-3}$ M |
| $CuSO_4 \cdot 5H_2O$ | $3 \times 10^{-9}$ M |
| $FeSO_4 \cdot 7H_2O$ | $1 \times 10^{-6}$ M |
| $Fe(NO_3)_3 \cdot 9H_2O$ | $2 \times 10^{-7}$ M |
| KCl | $4 \times 10^{-3}$ M |
| $MgSO_4 \cdot 7H_2O$ | $8 \times 10^{-4}$ M |
| NaCl | $1.05 \times 10^{-1}$ M |
| $Na_2HPO_4 \cdot 7H_2O$ | $3 \times 10^{-4}$ M |
| $NaH_2PO_4 \cdot 2H_2O$ | $6 \times 10^{-4}$ M |
| $Na_2SeO_3 \cdot 5H_2O$ | $3 \times 10^{-8}$ M |
| $Na_2SiO_3 \cdot 9H_2O$ | $1 \times 10^{-5}$ M |
| $(NH_4)_6Mo_7O_{24} \cdot 4H_2O$ | $3 \times 10^{-9}$ M |
| $NH_4VO_3$ | $5 \times 10^{-10}$ M |
| $NiSO_4 \cdot 6H_2O$ | $3 \times 10^{-10}$ M |
| $ZnSO_4 \cdot 7H_2O$ | $8 \times 10^{-7}$ M |
| inorganic iron source | $5 \times 10^{-5}$ M |

-continued

| | |
|---|---|
| L-Arg | $8 \times 10^{-4}$ M |
| L-Cys HCl.H$_2$O | $3 \times 10^{-4}$ M |
| L-Gln | $5 \times 10^{-3}$ M |
| L-His HCl.H$_2$O | $2 \times 10^{-4}$ M |
| L-Hydroxy-Pro | $1 \times 10^{-4}$ M |
| L-Ile | $6 \times 10^{-4}$ M |
| L-Leu | $6 \times 10^{-4}$ M |
| L-Lys HCl | $8 \times 10^{-4}$ M |
| L-Met | $1 \times 10^{-3}$ M |
| L-Phe | $3 \times 10^{-4}$ M |
| L-Thr | $6 \times 10^{-4}$ M |
| L-Trp | $6 \times 10^{-5}$ M |
| L-Tyr (diNa$^+$)2H$_2$O | $3 \times 10^{-4}$ M |
| L-Val | $6 \times 10^{-4}$ M |
| L-Ala | $2 \times 10^{-5}$ M |
| L-Asn.H$_2$O | $3 \times 10^{-4}$ M |
| L-Asp | $2 \times 10^{-5}$ M |
| L-Glu | $2 \times 10^{-5}$ M |
| Gly | $3 \times 10^{-5}$ M |
| L-Pro | $2 \times 10^{-4}$ M |
| L-Ser | $3 \times 10^{-4}$ M |
| Glutathione | $1 \times 10^{-6}$ M |
| Putrescine 2HCl | $3 \times 10^{-7}$ M |
| Biotin | $3 \times 10^{-8}$ M |
| D-Ca pantothenate | $2 \times 10^{-5}$ M |
| Folic acid | $6 \times 10^{-6}$ M |
| Folinic acid (Ca$^+$).5H$_2$O | $1 \times 10^{-6}$ M |
| Niacinamide (Nicotinamide) | $3 \times 10^{-5}$ M |
| p-Aminobenzoic acid | $3 \times 10^{-6}$ M |
| Pyridoxal HCl | $1 \times 10^{-5}$ M |
| Pyridoxine HCl | $3 \times 10^{-7}$ M |
| Riboflavin | $8 \times 10^{-7}$ M |
| Thiamine HCl | $9 \times 10^{-6}$ M |
| Vitamin B12 | $3 \times 10^{-7}$ M |
| D-Glucose | $2 \times 10^{-2}$ M |
| Na Pyruvate | $1 \times 10^{-3}$ M |
| Adenine | $1 \times 10^{-6}$ M |
| Hypoxanthine (Na$^+$) | $7 \times 10^{-6}$ M |
| Thymidine HCl | $1 \times 10^{-5}$ M |
| Choline chloride | $1 \times 10^{-4}$ M |
| Ethanolamine HCl | $2 \times 10^{-5}$ M |
| i-Inositol | $1 \times 10^{-4}$ M |
| Linoleic acid | $1 \times 10^{-7}$ M |
| Lipoic acid | $2 \times 10^{-7}$ M |
| HEPES | $2.5 \times 10^{-2}$ M |
| NaOH | $1.23 \times 10^{-2}$ M |
| NaHCO$_3$ | $3 \times 10^{-3}$ M |
| Insulin | $8.4 \times 10^{-7}$ M |
| Modified Polyurethane Synthetic Growth Factor comprising oxyethylene-based diols or polyol | $1.7 \times 10^{-6}$ M | units on which at least some of the hydroxy groups have been capped with polyisocyanate wherein the isocyanates of said polyisocyanates have been modified by an isocyanate (NCO) reactive functional group and wherein said modified polymer has a free functional group consisting of sulfhydryl or amino.

2. The nutrient medium of claim 1 in which the inorganic iron source is ferric sulfate.

3. The nutrient medium of claim 1 in which said inorganic iron source is ferric citrate or ferrous fumarate.

4. The nutrient medium of claim 1 in which the modified polyurethane synthetic growth factor is a sulfhydryl derivative of the polyurethane prepolymer base.

5. The nutrient medium of claim 4 in which the modified polyurethane synthetic growth factor is a cysteamine-modified polyurethane derivative.

6. The nutrient medium of claim 4 in which the modified polyurethane synthetic growth factor is a cysteine-modified polyurethane derivative.

7. The nutrient medium of claim 7 in which the modified polyurethane synthetic growth factor is a thiopropionic acid-modified polyurethane derivative.

8. The nutrient medium of claim 1 in which the modified polyurethane synthetic growth factor is a sulfonic acid derivative of the polyurethane prepolymer base.

9. The nutrient medium of claim 12 in which the modified polyurethane synthetic growth factor is a taurine-modified polyurethane derivative.

10. The nutrient medium of claim 1 which is supplemented with serum or another biological extract, or with defined proteins.

11. The nutrient medium of claim 10 in which said serum or extract is present as up to about one percent of the medium by volume.

12. The nutrient medium of claim 10 in which said proteins are selected from albumin, transferrin, fibronectin, vitronectin, fibroblast growth factor, epidermal growth factor, platelet-derived growth factor, interleukin-1, interleukin-2 and interleukin-6.

* * * * *